(12) United States Patent
Comaniciu et al.

(10) Patent No.: US 7,707,169 B2
(45) Date of Patent: Apr. 27, 2010

(54) SPECIFICATION-BASED AUTOMATION METHODS FOR MEDICAL CONTENT EXTRACTION, DATA AGGREGATION AND ENRICHMENT

(75) Inventors: Dorin Comaniciu, Princeton Junction, NJ (US); Peiya Liu, East Brunswick, NJ (US); Sridharan Palanivelu, Monmouth Jct., NJ (US)

(73) Assignee: Siemens Corporation, Iselin, NJ (US)

( * ) Notice: Subject to any disclaimer, the term of this patent is extended or adjusted under 35 U.S.C. 154(b) by 378 days.

(21) Appl. No.: 11/143,317

(22) Filed: Jun. 2, 2005

(65) Prior Publication Data

US 2006/0005139 A1 Jan. 5, 2006

Related U.S. Application Data

(60) Provisional application No. 60/578,813, filed on Jun. 10, 2004.

(51) Int. Cl.
*G06F 7/00* (2006.01)
(52) U.S. Cl. .................................................. 707/602
(58) Field of Classification Search .................. 707/102
See application file for complete search history.

(56) References Cited

U.S. PATENT DOCUMENTS

| | | | |
|---|---|---|---|
| 6,078,914 A * | 6/2000 | Redfern | 707/3 |
| 6,424,996 B1 * | 7/2002 | Killcommons et al. | 709/206 |
| 6,510,253 B1 * | 1/2003 | Yamada | 382/300 |
| 7,191,183 B1 * | 3/2007 | Goldstein | 707/101 |
| 7,233,938 B2 * | 6/2007 | Carus et al. | 707/1 |
| 7,289,997 B1 * | 10/2007 | Kita et al. | 707/100 |
| 2002/0112114 A1 * | 8/2002 | Blair et al. | 711/100 |
| 2002/0165717 A1 * | 11/2002 | Solmer et al. | 704/256 |
| 2002/0169788 A1 * | 11/2002 | Lee et al. | 707/104.1 |
| 2003/0055835 A1 * | 3/2003 | Roth | 707/102 |
| 2003/0140311 A1 * | 7/2003 | Lemon et al. | 715/513 |
| 2003/0233250 A1 * | 12/2003 | Joffe et al. | 705/2 |
| 2004/0172297 A1 * | 9/2004 | Rao et al. | 705/2 |
| 2005/0043620 A1 * | 2/2005 | Fallows et al. | 600/437 |
| 2005/0063575 A1 * | 3/2005 | Ma et al. | 382/128 |
| 2005/0192844 A1 * | 9/2005 | Esler et al. | 705/3 |
| 2006/0282447 A1 * | 12/2006 | Hollebeek | 707/101 |

OTHER PUBLICATIONS

Alcamo P et al, "An XML Based Environment in Support fo the Overall KDD Process", *FQAS*, 2000, pp. 413-424.

* cited by examiner

*Primary Examiner*—Don Wong
*Assistant Examiner*—Michael Le

(57) ABSTRACT

A method for knowledge generation from raw medical records uses XML-based specifications. The method includes content extraction, data aggregation and data enrichment. The method operates on various sources of medical data including financial data, clinical documents and medical images.

20 Claims, 6 Drawing Sheets

FIG. 5

```
...
509 ─── <Extraction>
             <Target Table Name="Encounters" DataSource="Expanded IMS Schema">
                 <Field Name="Encounter_NO"    From – "EncountersView.Encounter_NO">
                 <Field Name="MedicalRecord_NO" From – "EncountersView.MedicalRecord_NO">...
             </TargetTable>
510 ─── <VirtualView Name="EncountersView" DataSource="LanVision">
             <ViewFieldNames>Encounter_NO, MedicalRecord_NO, ...</>
             <ViewDefinition> ... transformations... <ViewDefinition> ...
        </VirtualView>
549 ─── </Extraction>
550 ─── <Constraints>
             <TargetTable Name="Encounters" DataSource="Expanded IMS Schema">
                 <Field Name="MedicalRecord_NO"
                        ValuePattern="000{[1-9][1-9][1-9]/$Num}"  –MedicalRecord_NO with leading zeros–
                        CorrectedValuePattern="$Num"/> ...           --Remove leading zeros –
             </TargetTable>
        </Constraints>
570 ─── <RecordMerge>
571 ───     <Record ... if="... Linkage Matching Criteria..."  Action="Insert_if_Not_exist" ...>
572 ───     <Record ... if="... Linkage Matching Criteria..."  Action="Updat_if_Duplicate" ...> ...
        </RecordMerge>
```

500

SPECIFICATION-BASED AUTOMATION METHODS FOR MEDICAL CONTENT EXTRACTION, DATA AGGREGATION AND ENRICHMENT

CLAIM OF PRIORITY

This application claims priority to, and incorporates by reference herein in its entirety, pending U.S. Provisional Patent Application Ser. No. 60/578,813, filed Jun. 10, 2004.

FIELD OF THE INVENTION

The present invention relates to a specification-based automation method and system for a knowledge generation process. More specifically, the method and system relate to data collection by content extraction, data aggregation and data enrichment from various original/intermediate data sources including databases, clinical documents and medical images. The methods are used to automate the overall process of knowledge generation by integrating the various data both vertically and horizontally for further knowledge applications. The specification-based methods provide a powerful mechanism to cope with the complexity and varieties of data sources in content extraction, data normalization, generation and enrichment.

BACKGROUND OF THE INVENTION

Many data-intensive applications require the enrichment of information from original data sources. That enriched information must be obtained through a knowledge generation process that may include initial data collection among different sources, data normalization and aggregation, and final data enrichment. Currently used techniques for obtaining such enriched information are manual, without seemingly integrated methods for automation. The methods used in current general knowledge generation processes are frequently content-specific, dealing with particular data sets on hand.

Furthermore, the interfaces used in data collection (or content extraction), data aggregation and enrichment methods are idiosyncratic. The manual process or content-specific application methods therefore have limitations in integrating the tasks of extracting content, aggregating data, and enriching data from many different sources and various intermediate content. Thus, there are difficulties in automating the overall knowledge generation process.

Advanced structured information representation and processing technologies, particularly XML (Extensible Markup Language)-related technologies, have become important in streamlining the knowledge generation process. Specification-based methods provide more flexible ways to integrate the processing of data from complex and various data sources in the knowledge generation process. For example, in "XML as a Unifying Framework for Inductive Databases," Rosa Meo and Giuseppe Psaila (book chapter from "XML Data Management: Native XML and XML-Enabled Database Systems," A. Chaudhri, A. Rashid, R. Zicari (eds.) (Addison-Wesley 2003)), there is proposed an XML data model called XDM for inductive databases to support mining-type data enrichment tasks. In "An XML Based Environment in Support of Overall KDD Process," P. Alcamo, F. Domenichini and F. Turni, the authors propose an XML-based environment to support an overall KDD (Knowledge Discovery in Database) process. Those methods are restricted to a particular type of data enrichment task. PMML (Predictive Model Markup Language) (at www.dmg.org) proposes an XML data model to describe various predictive data mining algorithms for exchanging mining results and models.

SUMMARY OF THE INVENTION

The present invention addresses the needs described above by providing an XML-based specification method for automating the entire knowledge generation process. Specifications are used to describe extraction rules for content extraction, migration rules for data aggregation and XML templates for data enrichment. The method encompasses a complete knowledge generation process from content extraction, data aggregation to data enrichment from various data sources including databases, clinical documents, and medical images. All automation methods are based on XML-based specifications to direct the various knowledge generation programs in the steps of the generation process. The methods provide more flexible and extensible ways to streamline the knowledge generation process, which is involved with many original/intermediate data sources and types for vertical and horizontal data integration.

In one embodiment of the invention, a method is provided for generating a structured content database from a diverse set of raw medical data. The method includes the steps of extracting content from the raw medical data according to mark-up language-based specifications, to produce a medical records database, aggregating records in the medical records database according to rules in a generalized specification-based language, to produce an aggregated medical records database, and enriching the aggregated medical records database using a generalized pipeline processing engine comprising mark-up language templates.

The step of extracting content may be performed according to XML-based specifications. The step of extracting content may further include extracting text-oriented content related to keywords and image-oriented content related to geometrical objects.

The step of extracting content may further comprise splitting documents in the raw medical data using XML-based specifications, and may further comprise indexing documents in the raw data using XML-based specifications.

The generalized specification-based language used in the aggregating step may be an XML-based language. The generalized specification-based language used in the aggregating step may further comprise a data extraction specification identifying at least one input data source and at least one output target table, a constraint differential description containing at least one data normalization operation; and at least one record merge rule for merging records to create the aggregated medical records database.

The data extraction specification may be based on a virtual database view of a transformation of the extracted content. In that case, the data extraction specification may further be based on a target table view of a data mapping of fields of the virtual database view to fields of the at least one output target table.

The mark-up language templates used in the step of enriching the aggregated medical records database may be XML-based templates. The mark-up language templates may perform at least one task chosen from a group consisting of structuring, transformation, hyper linking, query, discovering, mining and statistical analysis.

Another embodiment of the invention is a computer program product including a computer readable recording medium having recorded thereon a computer program comprising code means for, when executed on a computer, instructing the computer to control steps in the above method for generating a structured content database from a diverse set of raw medical data.

BRIEF DESCRIPTION OF THE DRAWINGS

FIG. 5 shows a fragment of an example specification according to one embodiment of the present invention.

DESCRIPTION OF THE INVENTION

In general, the system architecture and method of the present invention provide a specification-based automated transformation (1) from unstructured data to structured data, (2) from components to aggregated data, and (3) from aggregated data to derived (enriched) data or knowledge. The method operates on various initial or intermediate data sources such as databases, clinical documents and medical images to create a single knowledge-enriched information source.

The method of the present invention may be executed by one or more computer systems that include data memory for storage of data; a microprocessor for performing operations on the data; a signal input for receiving input data and logical code, and a signal output for outputting a signal relating to the data or the outcome of an operation on the data.

The method of the invention utilizes template specifications and XML-based data capturing. For example, the templates may be based on HL7/XML template processing, wherein HL7 (Health Level 7) is an ANSI standard for healthcare specific data exchange between computer applications. While the present invention is described with reference to XML-based templates and rules, templates and rules using other mark-up languages may be used without departing from the scope of the invention.

The system addresses difficulties created because the relevant medical content is frequently context-dependent; i.e., a priori information is needed to determine what is relevant in the medical data.

Figure 1:
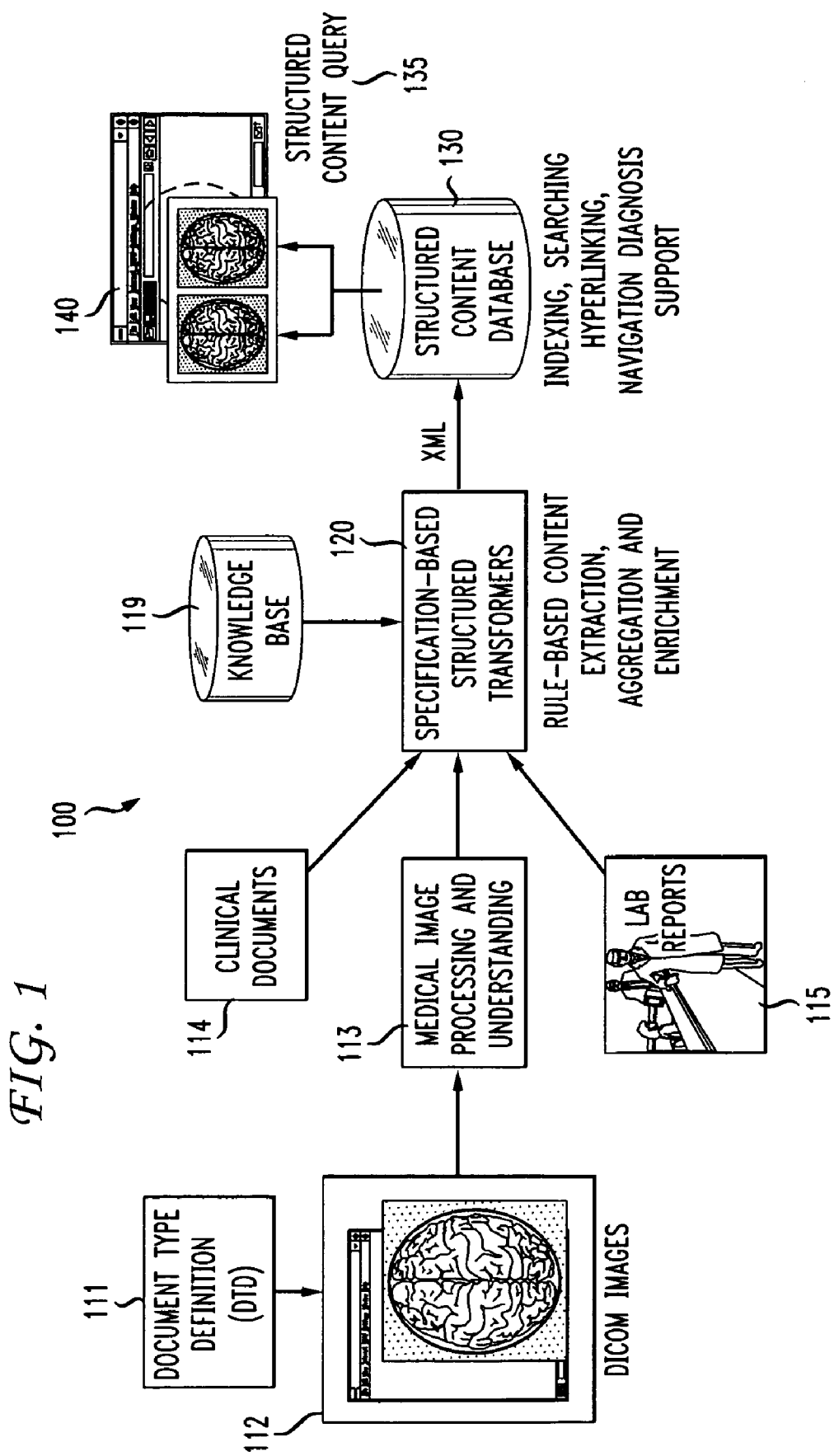
FIG. 1 is a schematic diagram showing an architecture of a specification-based knowledge generation process in accordance with one embodiment of the invention.

An architectural overview of the knowledge generation process 100 of the invention is illustrated in FIG. 1. In that architecture, the content of raw medical data including images, medical documents and lab reports, etc., are extracted, aggregated and enriched, by various structured transformers based on formal specifications, to integrate the data vertically and horizontally for further knowledge applications.

For example, a DICOM (Digital Imaging and Communications in Medicine) MRI or CAT scan image 112, accompanied by a corresponding DTD (Document Type Definition) definition 111, is processed by a medical image processing and understanding module 113 before being transmitted to specification-based structured transformers 120. Similarly, lab reports 115 and other clinical documents 114 are transmitted to the structured transformers 120.

The specification-based structured transformers 120 are seamlessly integrated together by using an XML-based specification in an extensible way. The various structured transformers will be described in the following sections.

Utilizing a knowledge base 119, the structured transformers 120 perform specification-based content extraction, aggregation and enrichment, building and supplementing structured content database 130. The structured content database 130 provides the user with indexing, searching, hyper linking and navigation diagnostic support. For example, structured content queries 135 may be performed in the database 130, yielding search results 140.

The medical content extraction and structuring portion of the present invention will now be described. It comprises content extraction, document bursting and indexing. The content extractor, document burster and structured indexer are based on rule specifications. The rules specify the location, string patterns and contexts of the target content to be extracted. The rules also specify content-based document splitting for multiple pages, and indexing.

Depending on the medical device used and how it is configured, raw medical data is generated in many document and image formats such as WinWord, TIFF, PCL, etc. Many formats can be transformed into a few standard formats such as PDF (for documents) or DICOM format (for images) for further content acquisition.

Figure 2:
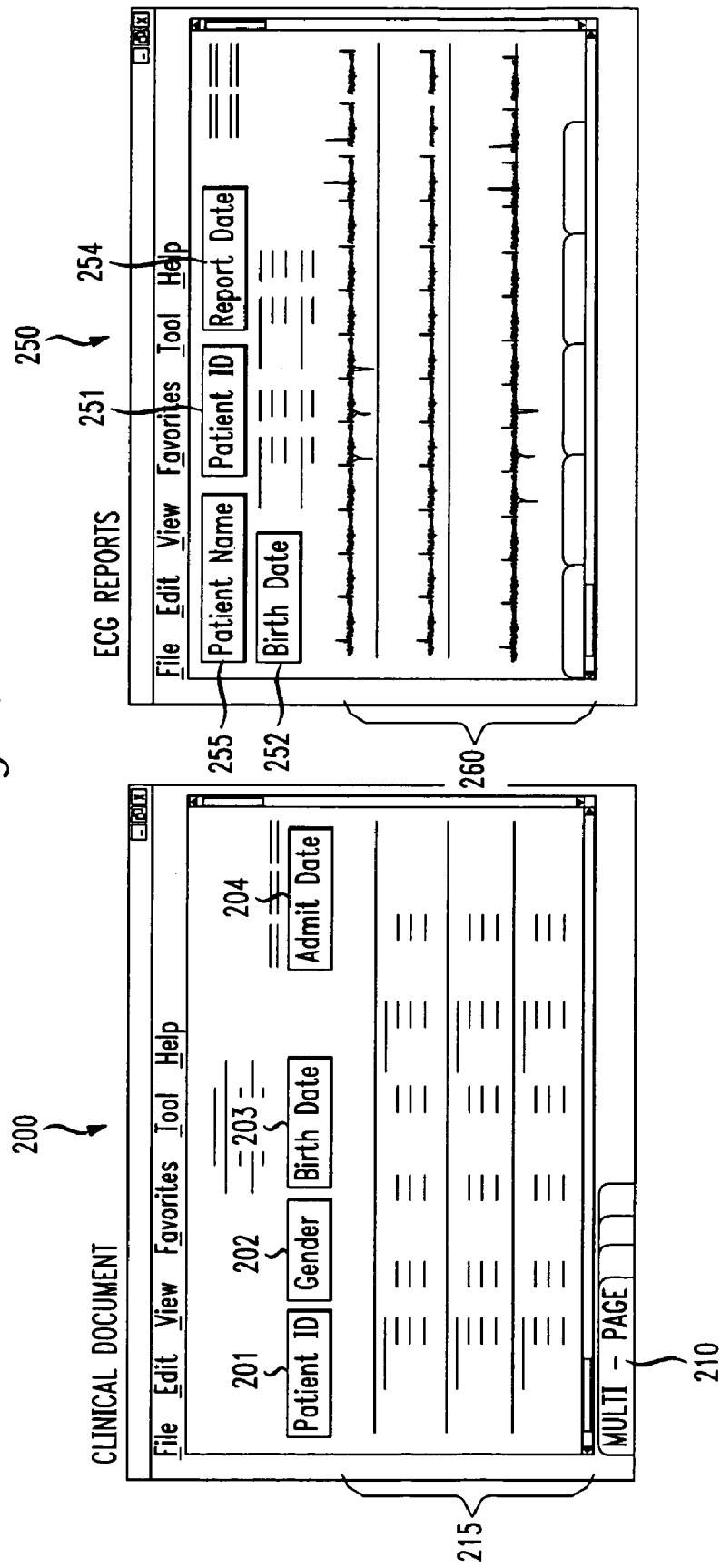
FIG. 2 shows exemplary medical documents from which data is extracted in the method of the present invention.

FIG. 2 shows two example medical documents 200, 250 that have been annotated to show information to be extracted. Document 200 is a first page of a clinical report in a text format containing medical and other information about a patient including patient ID 201, patient gender 202, patient birth date 203 and an admission date 204. Additional information 210 at the bottom of the page indicates that the document 200 is a multipage document. The main body 215 of the document contains the clinical data formatted in a human-readable table.

Document 250 contains ECG (electrocardiogram) information 260 in graphical format. In addition, the document contains patient information such as ID 251, birth date 252, report date 254 and patient name 255.

The documents may be loaded into the system in several ways. Multiple documents may be loaded in a batch process. Alternatively, the documents may be accepted in an on-line mode, either directly from the medical devices that generate the reports, or from health care provider data centers that may themselves aggregate the data before transmittal.

In general, the content may be placed into two categories based on the characteristics of the extraction methods that must be used. Specifically, the categories are image-oriented and textual-oriented.

The text-oriented content relates to keywords, which are self-contained and embedded in various formats of clinical documents such as PDF printouts, pure text files, WinWord, etc. An example of a text-oriented document 200 was described with reference to FIG. 2.

Image-oriented content is related to geometric objects. Extraction specifications by domain experts and automated CAD (computer-aided diagnosis) tools must label or name the objects. An example of image-oriented content 250 wherein ECG traces 260 comprise the geometric objects was also discussed with reference to FIG. 2.

In medical content extraction, a preferred embodiment of the present invention uses XML-based specifications in rules to describe the needed content location, string patterns or contexts to guide the extraction programs to get the needed content from the documents or images automatically.

Rules are also used to specify the "splitting" marker in the content for splitting documents having multiple pages. By using specifications, content-based document bursting methods of the invention can cope with the variety of splitting markers appearing in the content of multi-page medical documents. The results of content extraction are indexed and used as meta-data to the split documents.

Figure 3:
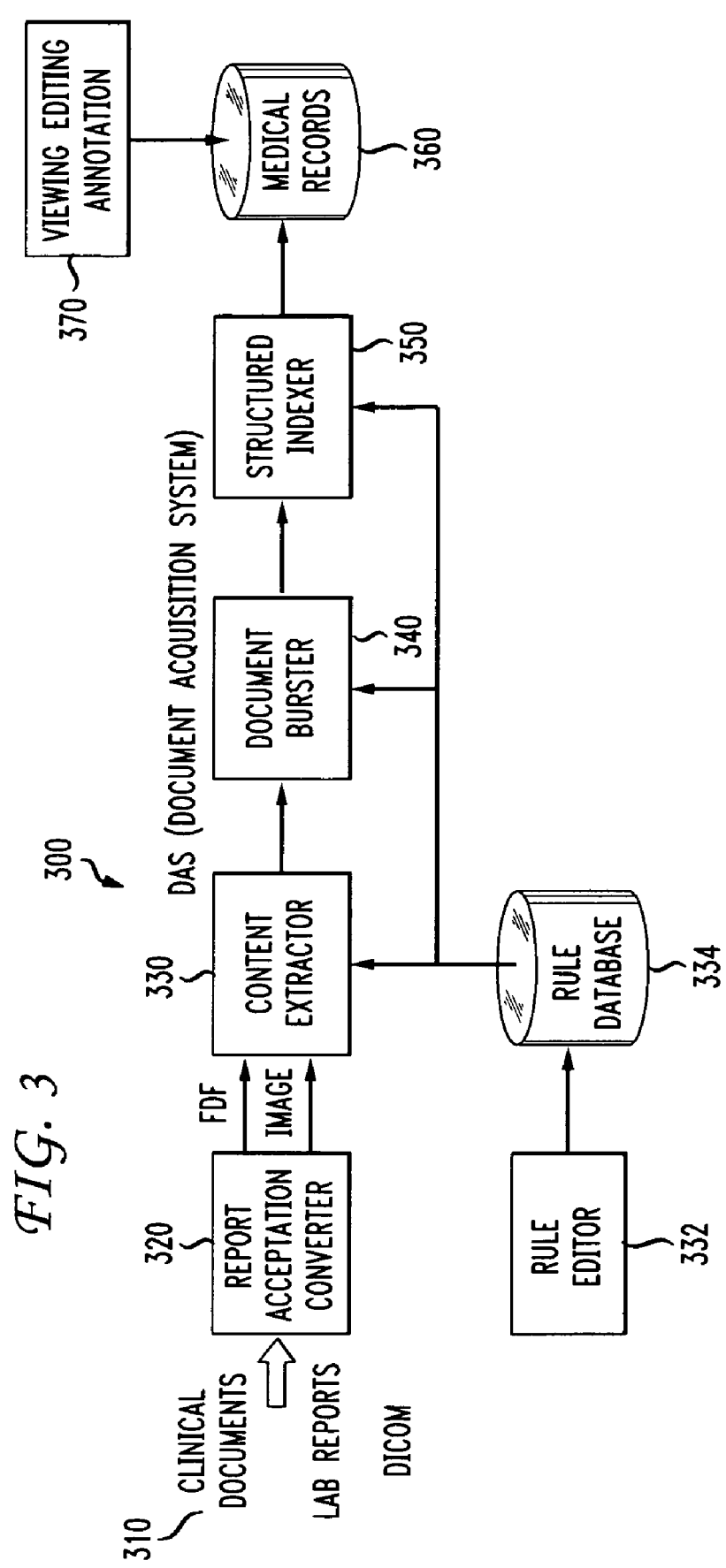
FIG. 3 is a schematic diagram showing a content extraction portion of a specification-based knowledge generation process in accordance with one embodiment of the invention.

An example of the medical content extraction and structuring portion 300 of the present invention is shown in FIG. 3. Image-oriented and text-oriented documents and reports 310 are accepted by a report acceptor/converter 320, that converts selected documents to more standard formats, such as PDF or DICOM, as described above. The documents, as processed by the report acceptor/converter, are transmitted to a content extractor 330.

As noted above, the content extractor 330 (as well as the document burster 340 and structured indexer 350) uses rules containing XML-based specifications to describe the needed content location, string patterns, geometry or contexts. The rules may be created or changed using a rule editor 332, and are stored in a rule database 334. The rules are used to guide the extraction programs to get the needed content from the documents or images automatically.

After processing by the content extractor 330, the document is split by the document burster 340 into multiple pages according to content-based bursting rules. A structured indexer 350 indexes and transforms the content. The content extractor 330, document burster 240 and structured indexer 350 are collectively referred to herein as the data acquisition system (DAS). The resulting extracted content is stored in a medical records database 360. The database is accessible to user interfaces 370 for viewing, editing and annotation. The interface 370 may be based on any relational database for accessing the documents.

Figure 4:
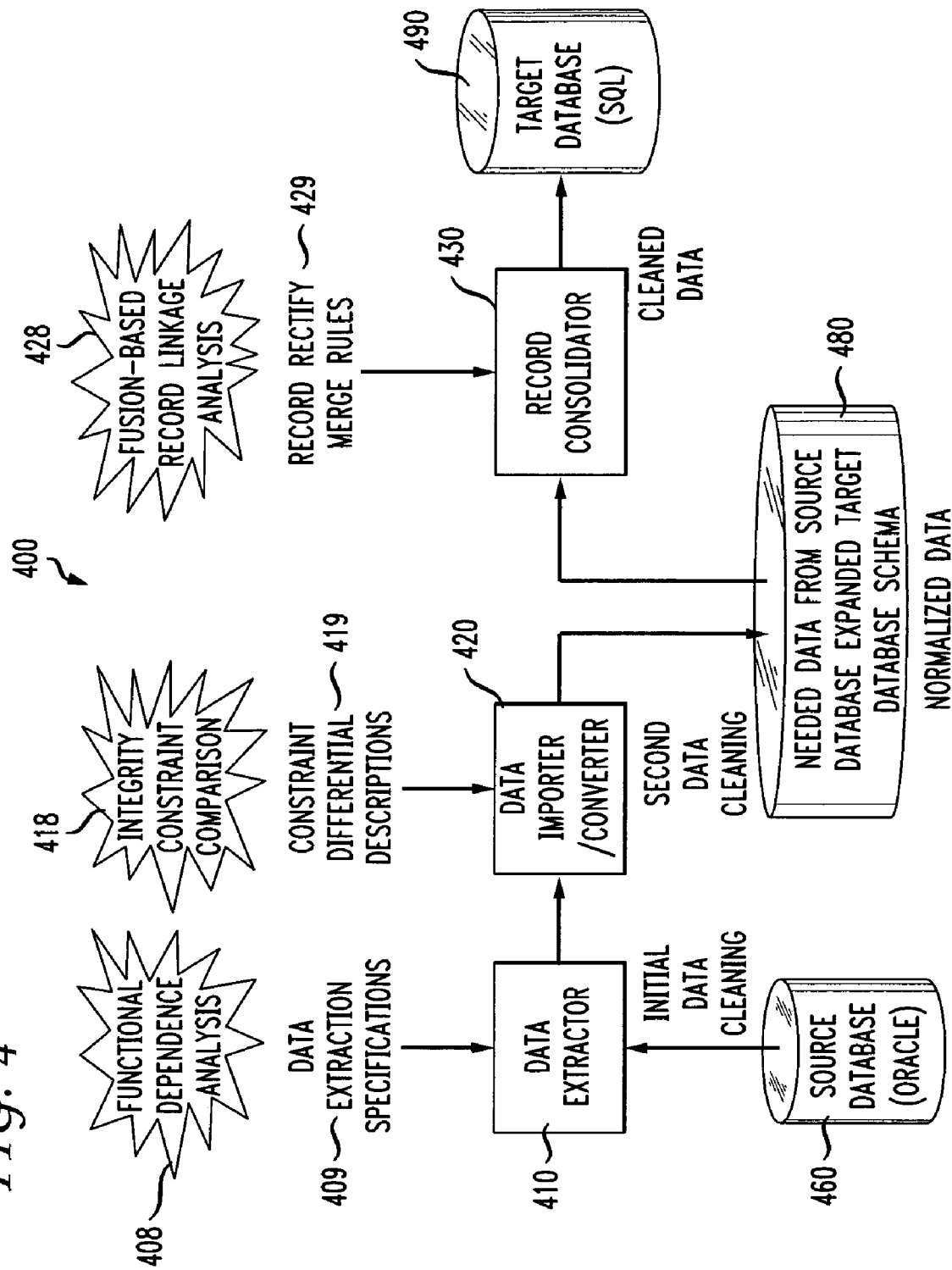
FIG. 4 is a schematic diagram showing a data aggregation portion of a specification-based knowledge generation process in accordance with one embodiment of the invention.

After content has been extracted from the subject documents as described above, the resulting data is aggregated using the data aggregation system and method of the present invention. The data aggregation system 400, shown in FIG. 4, is based on specifications written in DMSL (Data Migration Specification Language). A description of an example fragment of a specification written in DMSL is set forth below. The system utilizes rigorous database analysis techniques and generalized specification-based tools for automating data migration from the source medical records relational database 460 (in this example an Oracle database) into one single expanded database 480 with high quality cleaned data.

The data aggregation technique of the present invention uses several tools in migrating the data. First, the technique performs functional dependence analysis 408. In that analysis, a data extractor 410 conducts initial data cleaning on data from the source database 460. The data extractor extracts data from the database based on data extraction specifications 409 in DMSL. The data extraction specifications 409 are based on virtual database views of data source transformation and target table views of data mapping from virtual view table fields to target table fields.

An integrity constraint comparison 418 is a second step of the data migration portion of the invention. A data importer/converter 420 imposes database integrity constraints to constrain data values based on constraint differential descriptions 419, also in DMSL. The constraint differential descriptions relate to the database integrity constraint transformation from one data source to another source. After undergoing the second data cleaning by the data importer/converter 420, the normalized data is stored in database 480.

A fusion-based record linkage analysis 428 is a third step of the data migration. A record consolidator 430 merges records from the database 480 based on record rectify/merge rules 429, also in DMSL. The record rectify/merge rules 429 are concerned with record linkage descriptions based on "if-then-action"-type instructions. The resulting cleaned data is stored in the target relational database 490 (in this example an SQL server).

As noted above, the DMSL is a formal language used to describe rules for the data aggregation specifications, including functional dependence analysis 408, integrity constraint comparison 418 and fusion-based record linkage analysis 428. The DMSL is a language used to describe user-definable specifications to guide the migration and importing tools in performing actions in the database migration process.

An example fragment of a specification written in DMSL is shown in FIG. 5. The data extraction specification includes three parts: (1) data extraction specifications 509 including input data sources described in XML tag "<VirtualView>" 510, which may be a transformed view of original tables; and (2) constraint specifications 549 including output target tables in XML tag "<TargetTable>" 550, and (3) record merge specifications 570.

The constraint specifications describe all necessary data normalization operations and integrity constraints. Examples of normalization operations about data values are: format change, range adjust, modification, transformation and value translation. Integrity constraint specifications deal with addition, deletion and modification of database integrity constraints.

The record merge specifications describe how to merge the record sets between databases in XML tag <RecordMerge> 570 by using "if-then-action" rules 571, 572. The common database operations such as insertion, deletion and update are actually the degenerated cases of those DSML-based specifications for merging two homogeneous databases without needs of data normalization and integrity constraint changes.

Figure 6:
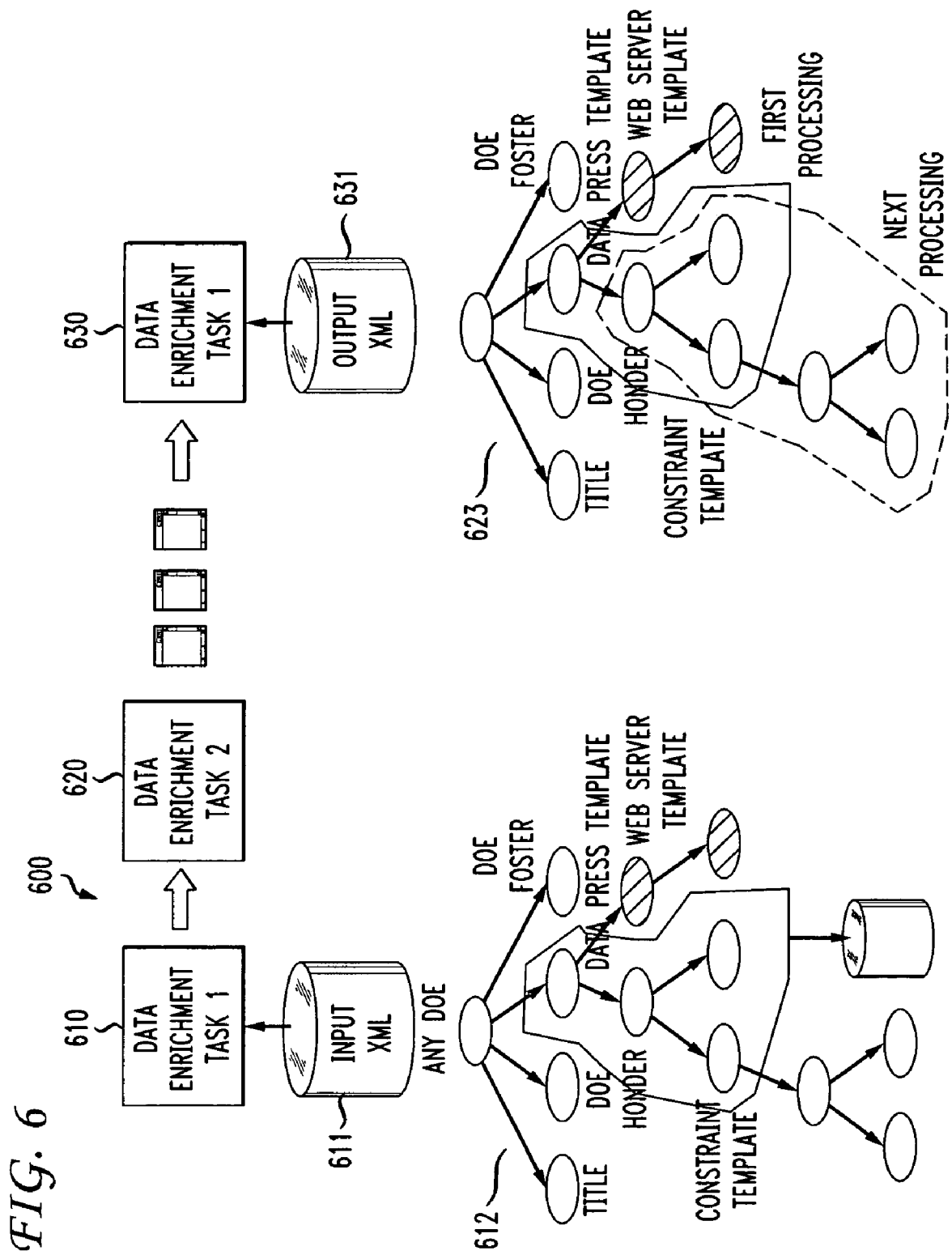
FIG. 6 is a schematic diagram showing a data enrichment portion of a specification-based knowledge generation process in accordance with one embodiment of the invention.

The extracted and aggregated data is then enriched using the data enrichment environment 600 of the present invention, shown in FIG. 6. Data enrichment tasks 610, 620, 630 relate to structuring data, data transformation, hyperlinking, queries, knowledge discovering, data mining, or statistical analysis, etc., for deriving additional information. Often a set of data enrichment tasks is required to be executed in a particular sequence and context in order to achieve the desired enriched information.

The tasks 610, 620, 630 are uniformly formalized as a sequence of "XML template computing," which uses input XML templates such as input XML 611 as specifications for data enrichment task execution and contexts. As such, the tasks implement the Artificial Intelligence concept of "programs as data" in XML. The input XML templates may comprise an in-memory XML DOM (document object model) tree such as tree 612. The XML templates include primitive elements such as variables, conditional logic, SQL/SOAP, top-level parameters, Javascript and XML/XSLT references.

The execution sequence and contexts of tasks are specified in unique XML Enrichment Templates. An XML Template Composition Engine is designed as a generalized pipeline processing engine to interpret the enrichment tasks based on specifications in the XML Enrichment Templates. The generalized pipeline processing engine is based on the composition of structured data in addition to the pipeline processing of functional data. The Template Composition Engine is extensible and customizable.

The resulting enriched information 631 is in the common XML form of association models (rules, clusters, trees, etc.), functional models, structural models and behavioral models 632.

The foregoing Detailed Description is to be understood as being in every respect illustrative and exemplary, but not restrictive, and the scope of the invention disclosed herein is not to be determined from the Description of the Invention, but rather from the Claims as interpreted according to the full breadth permitted by the patent laws. For example, while the technique is described primarily for use in connection with the extraction, aggregation and enrichment of medical data, the technique of the invention may be used in dealing with other types of data. It is to be understood that the embodiments shown and described herein are only illustrative of the principles of the present invention and that various modifications may be implemented by those skilled in the art without departing from the scope and spirit of the invention.

What is claimed is:

1. A method for structuring diverse medical data as a database comprising:
    extracting content from the diverse medical data comprising:
        generating Extensible Markup Language (XML)-based extraction rules for each type of medical data based on predetermined information from the medical data document type;
        converting each medical data document type into one or more standard document types, wherein each standard document type includes text and image object relevant content;
        extracting the relevant content from each standard document type using the XML-based extraction rules associated with the medical data document type as an XML syntax;
        indexing the extracted relevant content; and
        storing the indexed relevant content;
    aggregating the stored indexed relevant content comprising:
        creating data migration language extraction rules;
        extracting the stored indexed relevant content using the data extraction rules;
        creating data migration language constraint differential rules;
        normalizing the extracted indexed relevant content using the constraint differential rules;
        storing the normalized relevant content;
        creating data migration language record/rectify merge rules;
        consolidating the normalized relevant content using the record/rectify merge, rules; and
        storing the consolidated relevant content;
    enriching the stored consolidated relevant content comprising:
        creating one or more XML templates; and
        sequentially processing the consolidated relevant content using the one or more XML templates into models.

2. The method according to claim 1 wherein the standard document types include pdf and Digital Imaging and Communications in Medicine (DICOM) standards.

3. The method according to claim 1 wherein the extraction rules specify relevant content location, string patterns, and contexts where to extract the text and/or image object content.

4. The method according to claim 1 wherein aggregating further comprises mapping data from each standard format to provide for data extraction and data loading.

5. The method according to claim 1 wherein the data extraction rules are created using Data Migration Specification Language (DMSL).

6. The method according to claim 1 wherein aggregating further comprises performing a functional dependence analysis on the indexed relevant content.

7. The method according to claim 1 wherein aggregating further comprises performing an integrity constraint comparison on the indexed relevant content.

8. The method according to claim 1 wherein aggregating further comprises performing a record linkage analysis on the indexed relevant content.

9. The method according to claim 1 wherein the data migration language uses XML tags.

10. The method according to claim 1 wherein the models include associated models, functional models, structural models and behavioral models.

11. A computer program product comprising a computer readable recording medium having recorded thereon a computer program comprising code means for, when executed on a computer, instructing the computer to control steps in a method for structuring diverse medical data as a database comprising:
    extracting content from the diverse medical data comprising:
        generating Extensible Markup Language (XML)-based extraction rules for each type of medical data based on predetermined information from the medical data document type;
        converting each medical data document type into one or more standard document types, wherein each standard document type includes text and image object relevant content;
        extracting the relevant content from each standard document type using the XML-based extraction rules associated with the medical data document type as an XML syntax;
        indexing the extracted relevant content; and
        storing the indexed relevant content;
    aggregating the stored indexed relevant content comprising:
        creating data migration language extraction rules;
        extracting the stored indexed relevant content using the data extraction rules;
        creating data migration language constraint differential rules;
        normalizing the extracted indexed relevant content using the constraint differential rules;
        storing the normalized relevant content;
        creating data migration language record/rectify merge rules;
        consolidating the normalized relevant content using the record/rectify merge rules; and
        storing the consolidated relevant content;
    enriching the stored consolidated relevant content comprising:
        creating one or more XML templates; and
        sequentially processing the consolidated relevant content using the one or more XML templates into models.

12. The computer program product according to claim 11 wherein the standard document types include pdf and Digital Imaging and Communications in Medicine (DICOM) standards.

13. The computer program product according to claim 11 wherein the extraction rules specify relevant content location, string patterns, and contexts where to extract the text and/or image object content.

14. The computer program product according to claim 11 wherein aggregating further comprises mapping data from each standard format to provide for data extraction and data loading.

15. The computer program product according to claim 11 wherein the data extraction rules are created using Data Migration Specification Language (DMSL).

16. The computer program product according to claim 11 wherein aggregating further comprises performing a functional dependence analysis on the indexed relevant content.

17. The computer program product according to claim 11 wherein aggregating further comprises performing an integrity constraint comparison on the indexed relevant content.

18. The computer program product according to claim 11 wherein aggregating further comprises performing a record linkage analysis on the indexed relevant content.

19. The computer program product according to claim 11 wherein the data migration language uses XML tags.

20. The computer program product according to claim 11 wherein the models include associated models, functional models, structural models and behavioral models.

* * * * *